(12) United States Patent
Matheny

(10) Patent No.: US 8,784,891 B2
(45) Date of Patent: *Jul. 22, 2014

(54) COMPOSITIONS FOR REGENERATING DEFECTIVE OR ABSENT MYOCARDIUM

(71) Applicant: Francis Law Group, Alameda, CA (US)

(72) Inventor: Robert G Matheny, Norcross, GA (US)

(73) Assignee: CorMatrixCardiovascular, Inc., Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,805

(22) Filed: Jan. 2, 2013

(65) Prior Publication Data

US 2013/0129831 A1 May 23, 2013

Related U.S. Application Data

(62) Division of application No. 11/182,551, filed on Jul. 15, 2005, now Pat. No. 8,568,761.

(51) Int. Cl.
| | |
|---|---|
| A61K 48/00 | (2006.01) |
| A61L 27/36 | (2006.01) |
| A61L 27/40 | (2006.01) |
| A61K 38/17 | (2006.01) |
| A61K 35/54 | (2006.01) |
| A61L 27/38 | (2006.01) |
| A61K 35/38 | (2006.01) |
| A61K 35/34 | (2006.01) |
| A61K 38/18 | (2006.01) |
| A61K 9/00 | (2006.01) |

(52) U.S. Cl.
CPC .......... *A61K 35/34* (2013.01); *A61K 48/00* (2013.01); *A61L 27/3633* (2013.01); *A61L 27/40* (2013.01); *A61K 9/0019* (2013.01); *A61K 38/1741* (2013.01); *A61K 35/545* (2013.01); *A61L 27/3873* (2013.01); *A61K 35/38* (2013.01); *A61L 27/367* (2013.01); *A61K 38/1841* (2013.01); *A61L 27/3683* (2013.01); *A61L 2400/06* (2013.01)
USPC ........... 424/484; 424/423; 424/520; 424/551; 435/387

(58) Field of Classification Search
USPC .................. 424/484, 423, 520, 551; 435/387
See application file for complete search history.

(56) References Cited

U.S. PATENT DOCUMENTS

| | | | | |
|---|---|---|---|---|
| 5,275,826 | A * | 1/1994 | Badylak et al. | 424/551 |
| 6,096,347 | A * | 8/2000 | Geddes et al. | 424/551 |
| 6,206,931 | B1 * | 3/2001 | Cook et al. | 623/23.75 |
| 6,375,989 | B1 * | 4/2002 | Badylak et al. | 424/551 |
| 7,175,841 | B2 * | 2/2007 | Badylak et al. | 424/93.7 |
| 7,226,611 | B2 * | 6/2007 | Yura et al. | 424/423 |
| 8,409,625 | B2 * | 4/2013 | Badylak | 424/574 |
| 2004/0175366 | A1 * | 9/2004 | Badylak | 424/93.7 |
| 2005/0025838 | A1 * | 2/2005 | Badylak | 424/551 |

OTHER PUBLICATIONS

Junqueira et al., Basic Histology, Fifth Edition 1986 Lange Medical Publications, Los Altos California; pp. 266-267.*
Perets et al., Enhancing the vascularization of three-dimensional porous alginate scaffolds by incorporating controlled release basic fibroblast growth factor microspheres Journal of Biomedical Materials Research Part A vol. 65A, Issue 4, pp. 489-497, Jun. 15, 2003.*
Rosenblatt-Velin et al., J Clin Invest. Jul. 2005;115(7):1724-33. Epub Jun. 9, 2005. FGF-2 controls the differentiation of resident cardiac precursors into functional cardiomyocytes.*
Hecker et al., Engineering the heart piece by piece: state of the art in cardiac tissue engineering Mar. 2007, vol. 2, No. 2, pp. 125-144.*

* cited by examiner

*Primary Examiner* — Maria Leavitt
(74) *Attorney, Agent, or Firm* — Francis Law Group

(57) ABSTRACT

Compositions of the invention for regenerating defective or absent myocardium comprise an emulsified or injectable extracellular matrix composition. The composition may also include an extracellular matrix scaffold component of any formulation, and further include added cells, proteins, or other components to optimize the regenerative process and restore cardiac function.

10 Claims, 3 Drawing Sheets

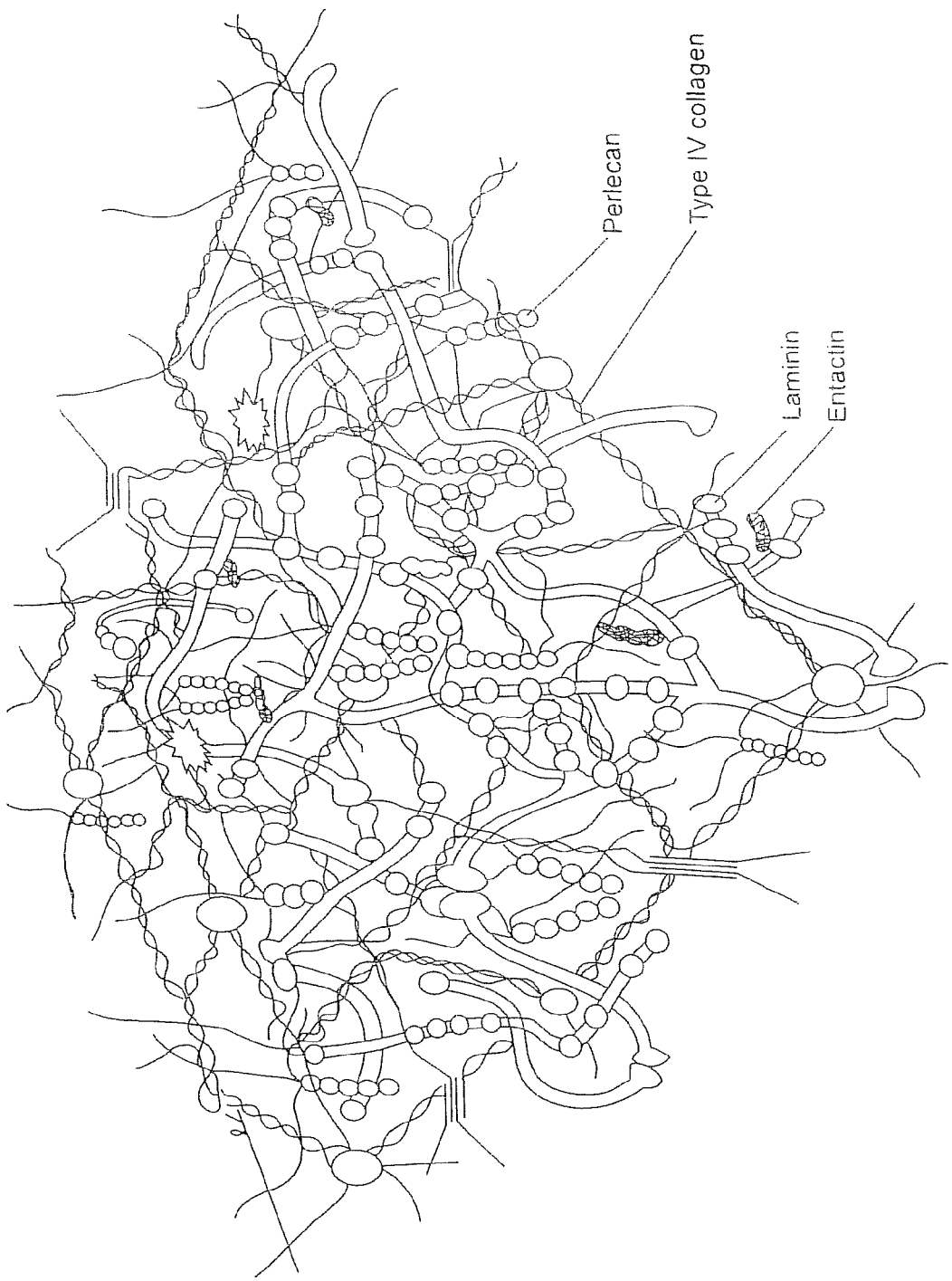

COMPOSITIONS FOR REGENERATING DEFECTIVE OR ABSENT MYOCARDIUM

CROSS-REFERENCE TO RELATED APPLICATIONS

This application is a Divisional Application of U.S. application Ser. No. 11/182,551, filed on Jul. 15, 2005, now U.S. Pat. No. 8,568,876.

FIELD OF THE INVENTION

The invention relates to tissue engineering generally, and more specifically to compositions and methods for regenerating defective or absent myocardium.

BACKGROUND OF THE INVENTION

Heart failure occurs in nearly 5 million people a year in the U.S. alone at a combined cost of about $40 billion annually for hospitalization and treatment of these patients. The results of all the effort and cost are disappointing with a 75% five year mortality rate for the heart failure victims. Treatments for chronic heart failure include medical management with pharmaceutical drugs, diet and exercise, transplantation for a few lucky recipients, and mechanical assist devices, which are costly and risk failure and infection. Thus the landscape for cardiac treatment is turning in recent years to transplantation of tissue or cells.

Medical researchers have transplanted human hematopoetic stem cells, mesenchymal stem cells, endothelial precursor cells, cardiac stem cells, and skeletal myoblasts or bone marrow cells to the myocardium, with however little or mixed success in satisfactory regeneration of the myocardium. Another protocol involved injecting transforming growth factor beta preprogrammed bone marrow stem cells to the myocardium, with greater success than transplantation of bone marrow stem cells alone, but without generation of contractile myocardium.

After myocardial infarction, injured cardiomyocytes are replaced by fibrotic tissue promoting the development of heart failure. On the basis that embryonic stem cells may be directed to differentiate into true cardiomyocytes, transplantation of embryonic stem cells to a site of myocardial infarction may yield success in myocardial tissue regeneration, though the experiments have not yet so proven. For a related challenge, to induce angiogenesis in ischemic myocardial tissue, transplanting endothelial progenitor cells, with or without angiogenic protein factors has been proposed to generate capillary blood vessels at the site of ischemia in the myocardium. As yet, the experiments to prove these theories have not worked sufficiently to be attempted in humans.

Meanwhile, typical structural abnormalities or damage to the heart that would lend itself to tissue regenerative therapies, were they available, include atrial septal defects, ventricular septal defects, right ventricular out flow stenosis, ventricular aneurysms, ventricular infarcts, ischemia in the myocardium, infarcted myocardium, conduction defects, conditions of aneurysmic myocardium, ruptured myocardium, and congenitally defective myocardium, and these defective conditions remain untreated in humans by any current tissue regenerative techniques.

Although tissue regeneration has been accomplished by transplantation in mammalian tissues such as the endocranium, the esophagus, blood vessels, lower urinary tract structures, and musculotendinous tissues, heart tissue regeneration by foreign tissue explant has remained a challenge. Recently, myocardium has been regenerated using xenogenic extracellular matrix patches in pigs and dogs, and the contractility achieved was at 90% of normal.

It would be beneficial for treatment of heart failure in humans to develop myocardium regenerative strategies using matrices and additives for optimizing the potential results. One problem exists in the preparation of extracellular scaffolds in that they must be non-immunogenic and thus acellular before implantation. Getting rid of the cells in the matrix may also inadvertently strip the scaffold of key bioactive proteins. In order to perform procedures to regenerate human myocardium with fidelity, compositions that mimic the function of extracellular matrices are provided below.

No experimentation has been conducted to date on regenerating mammalian myocardium using an emulsified or injectable extracellular matrix formulation. The only known experimental use of extracellular emulsions for tissue regeneration have been with gastroesophageal repair to prevent reflux and urinary bladder sphincter repair. Both of these experiments were conducted in non-human animals. Some veterinary use of extracellular matrix emulsions have been reported, but none of those uses were for the repair of myocardium. The disadvantage of using intact, non-emulsified extracellular matrix compositions such as patches or strips is that placement of the material requires open surgery, with its coordinate risk of infection, challenge of access to the site, and longer recovery for the patient post-procedure.

The present invention pioneers compositions and alternatives to prior art solutions for tissue regeneration to provide a biomedical composition (and methods using the composition) for regenerating defective or absent myocardium, particularly for use in humans.

SUMMARY OF THE INVENTION

An object of the invention is to provide a composition for regenerating defective or absent myocardium and restoring cardiac function.

Accordingly, a composition for regenerating defective or absent myocardium and restoring cardiac function comprising an emulsified or injectable extracellular matrix composition from a mammalian or synthetic source is provided.

Also, a composition for regenerating defective or absent myocardium and restoring cardiac function is provided comprising an extracellular matrix derived from a mammalian or synthetic source, said composition further comprising an additional component selected from the group of: a) a cell, b) a peptide, polypeptide, or protein, c) a vector having a DNA capable of targeted expression of a selected gene, and d) a nutrient, a sugar, a fat, a lipid, an amino acid, a nucleic acid, a ribo-nucleic acid, an organic molecule, an inorganic molecule, a small molecule, a drug, or a bioactive molecule.

Also provided is a composition for regenerating defective or absent myocardium and restoring cardiac function comprising at least a portion of an extracellular matrix scaffold derived from a mammalian source and also comprising an additional component selected from the groups consisting of: a) a plurality of synthetic extracellular matrix-like scaffold-forming molecules, b) a cell, c) a peptide, polypeptide, or protein, and d) a vector having a DNA capable of targeted expression of a selected gene, and e) a nutrient, a sugar, a fat, a lipid, an amino acid, a nucleic acid, a ribo-nucleic acid, an organic molecule, an inorganic molecule, a small molecule, a drug, or a bioactive molecule.

The invention further provides a method of regenerating defective myocardium and restoring cardiac function, comprising contacting said defective myocardium with a composition of the invention in an amount effective to regenerate the myocardium and restore cardiac function.

The invention also provides a method of inducing angiogenesis in myocardium at a site of ischemia, comprising contacting said ischemic myocardium with a composition of the invention in an amount effective to induce angiogenesis in the myocardium at the site of ischemia.

Further embodiments of the invention are described herein.

BRIEF DESCRIPTION OF THE DRAWINGS

FIG. 3 depicts a model of matrix scaffold structure including common collagen, proteoglycans, and glycoproteins.

DETAILED DESCRIPTION OF THE INVENTION

The invention is a composition that regenerates defective or absent myocardium and restores cardiac function. For this purpose, an emulsified or injectable extracellular matrix composition can be derived from a mammalian or synthetic source. The composition can further include added cells or protein or both. An extracellular matrix composition of any formulation can include also an additional component such as: a) a cell, b) a peptide, polypeptide, or protein, or c) a vector expressing a DNA of a bioactive molecule, and d) other additives like nutrients or drug molecules. One additional component can be used in the composition or several. The composition can be placed in contact with the defective or absent myocardium, resulting in myocardial tissue regeneration and restoration of contractility, conductivity, or function to the heart muscle. The invention appreciates the importance of the presence of some amount and form of an extracellular matrix, or extracellular matrix-like scaffold, as a framework for the essential activities of cell-cell, matrix-cell, protein-cell, and protein-protein interactions that form the dynamic tissue regenerative process in vivo, potentially optimized by the presence of added cells, proteins, or other bioactive components.

A composition to accomplish regeneration of myocardium needs to induce complex dynamic interactions and activities at the site of defect. The present invention provides a composition that creates an environment in vivo to allow these processes to occur. The processes needed to regenerate myocardium include specific phenotypic changes in stem cells that are recruited to the defective site, establishment of cell-cell connections, establishment of vascular supply at the site, beginning of normal tissue specific metabolism, limiting new growth once new tissue is made, coupling electric conduction from new cells to existing cells and pathways, and establishment of cell-extracellular matrix connections by way of cell adhesions to the matrix proteins.

The expectations for the extracellular matrix scaffold are that it will organize the cells into tissues, both by recruiting endogenous cells and using cells that have been provided as additional components in the composition. The extracellular matrix scaffold then coordinates the function of the newly recruited or added cells, allowing also for cell migration within the matrix. The matrix allows and provides for normal metabolism to the cells once the vascular supply delivering nutrients to the cells is established. Additionally, signal transduction pathways for growth, differentiation, proliferation and gene expression are established.

Figure 1:
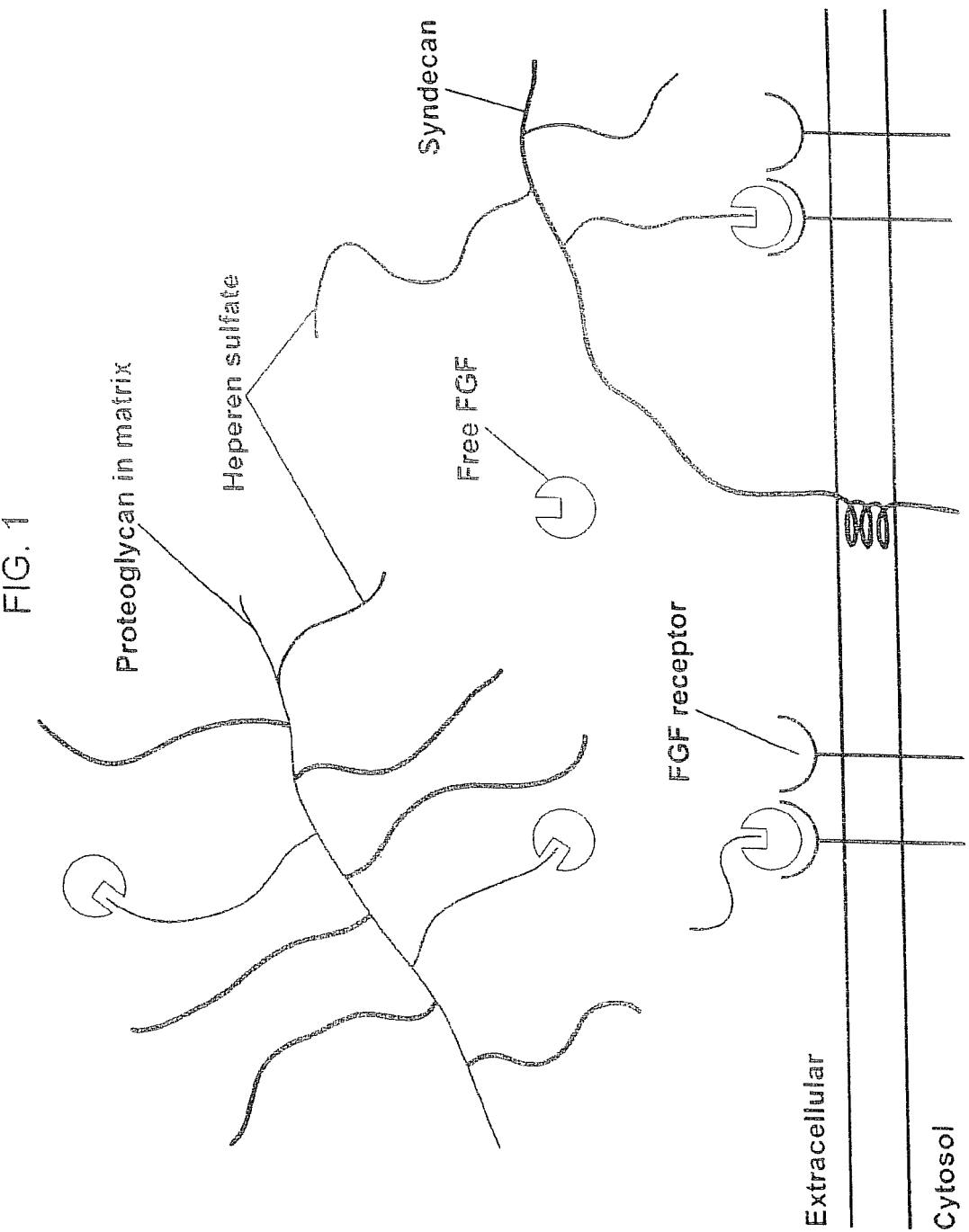
FIG. 1 depicts cell-ECM interaction through the matrix proteoglycans, glycoaminoglycans and growth factors.
Figure 2:
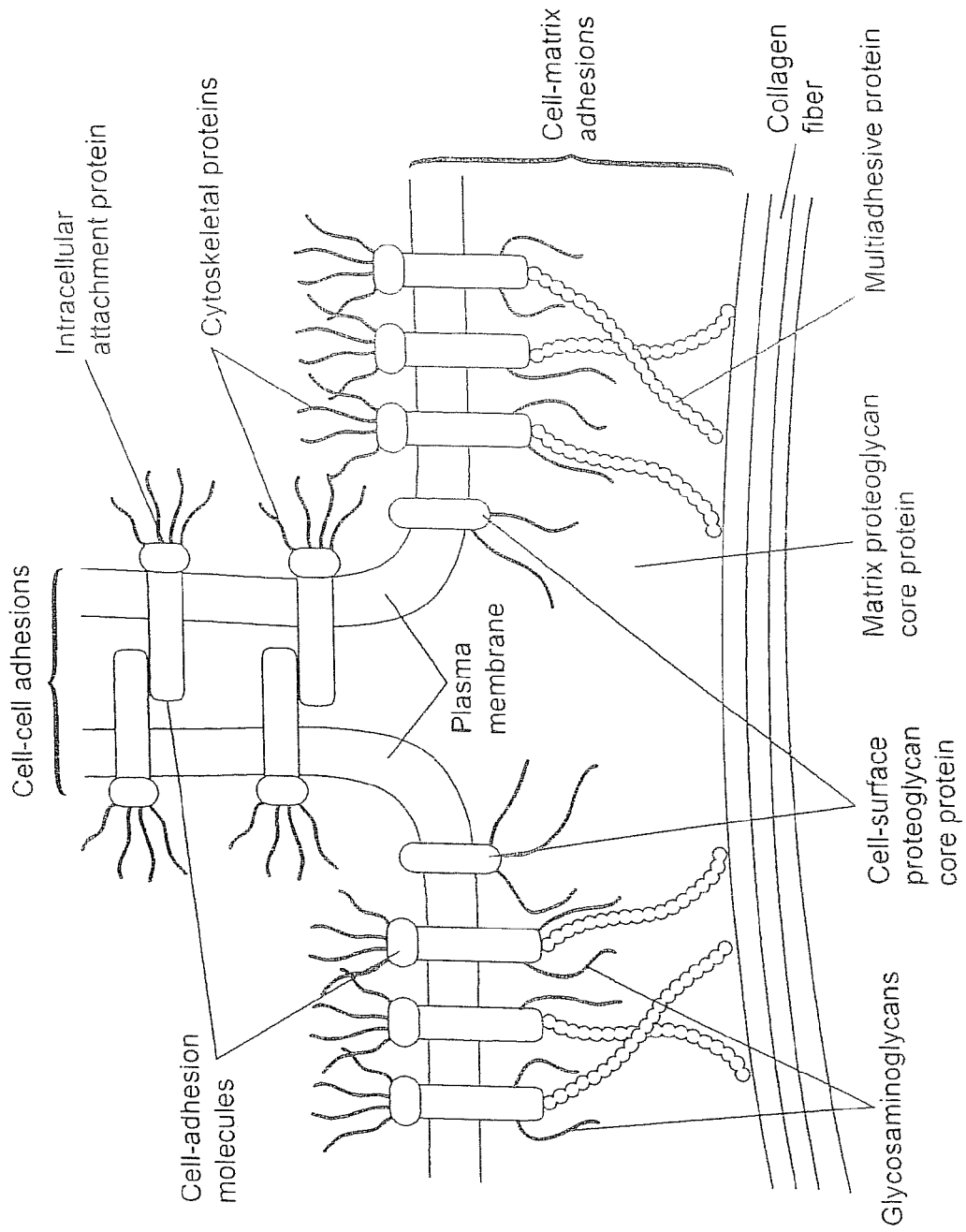
FIG. 2 depicts cell-cell adhesions, and cell-matrix adhesions through specific structural and functional molecules of the ECM.

The extracellular matrix of myocardium is complex. There is a three-dimensional architecture established with proteoglycan molecules, with available cytokines in the microenvironment. Cell movement occurs using focal adhesions, and eventually permanent cell adhesions occur called hemidesmosomes. Environmental signals are transmitted, including specific cell signals from growth factors on cell surfaces and disposed within the matrix framework as well. The matrix itself has structural components and functional components and the line between the two sometimes blurs because some of the moieties of structural components signal and trigger protein activation, and activation of nearby cells. See FIG. 1 for an illustration of signaling, FIG. 2 for depiction of cell-cell, protein-cell, and matrix-cell interactions, and FIG. 3 for a diagrammatic view of three-dimensional ECM scaffold.

There has been much research recently to elucidate the properties and function of the extracellular matrix: its protein make-up, and its role in the body. The extracellular matrix (ECM) is a scaffold matrix of polymerized "structural" proteins that fit into three groups: collagens, glycoproteins, and proteoglycans (which have glycosaminoglycan repeats throughout). These molecules actually polymerize to form the scaffold or matrix of proteins that exists in dynamic interaction with cells, and closely placed functional proteins (either on the cells, or bound to a structural protein).

Thus, the extracellular matrix also includes within its matrix scaffold "functional" proteins that interact with the structural proteins and with migrating or recruited cells, particularly stein cells in tissue regeneration. The matrix functional proteins also interact with protein expressing cells during the life and maintenance of the matrix scaffold itself as it rebuilds and maintains its components. Note that some proteins fall into both a structural protein classification and a functional protein classification, depending on the protein's configuration and placement in the whole matrix.

The extracellular matrix of myocardium is made up of collagen types I (which is predominant), III, IV, V, and VI, combined which are 92% of the dry weight of the matrix. Glycosaminoglycans (GAGs) include chondroitin sulfate A and B, heparan, heparin, and hyaluronic acid. Glycoproteins such as fibronectin and entactin, proteoglycans such as decorin and perlecan, and growth factors such as transforming growth factor beta (TGF-beta), fibroblast growth factor-2 (FGF-2) and vascular endothelial growth factor (VEGF), are key players in the activity of a myocardium regenerating matrix. Furthermore, the precise chemical constitution of the matrix appears to play a role in its function, including for example what collagen type is prevalent in the matrix, the pore size established by the matrix scaffold, the forces transmitted to adhesion molecules and mechanoreceptors in the cell membranes of cells at the matrix, and the forces directed from the three-dimensional environment (for example the gene expression in the three-dimensional matrix scaffold environment is very different than in a monolayer environment). Thus, the outcome of any tissue regenerative processes is determined by the structural and functional components of the matrix scaffold that form the basis of the regenerative process.

More specifically, when in early regenerative processes, circulating cells or added cells are directed, initial temporary cell adhesion processes occur that result in embryogenesis of the cells, morphogenesis of the cells, regeneration of cell form, eventual maintenance of the cell, possible motility to another site, and organogenesis that further differentiates the cell. Facilitating these early cell adhesion functions are cell adhesion molecules (CAMs). The CAMs are available either endogenously, or added as an additional component of the composition. CAMs are glycoproteins lodged in the surface of the cell membrane or transmembrane connected to cytoskeletal components of the cell. Specific CAMs include cadherins that are calcium dependent, and more than 30 types are known.

Also working as CAMs are integrins, which are proteins that link the cytoskeleton of the cell in which they are lodged to the extracellular matrix or to other cells through alpha and beta transmembrane subunits on the integrin protein. See FIG. 2 for an illustration of these interactions. Cell migration, embryogenesis, hemostatis, and wound healing are so facilitated by the integrins in the matrix. Syndecans are proteoglycans that combine with ligands for initiating cell motility and differentiation. Immunoglobins provide any necessary immune and inflammatory responses. Selectins promote cell-cell interactions.

Specific requirements for the scaffold component of the invention, whether a native scaffold prepared for introduction into a mammal, or a synthetic scaffold formed by synthetic polymerizing molecules, or a combination of the two, are that the scaffold must be resorbable over time as the tissue regeneration ensues, and this resorbtion is at an appropriate degradation rate for optimal tissue regeneration and absence of scar tissue formation.

The extracellular matrix scaffold is preferably non-toxic and provides a three-dimensional construction at the site of defect in the myocardium (once delivered to the site). The matrix scaffold is required to have a high surface area so that there is plenty of room for the biological activities required of the tissue regeneration process. The scaffold must be able to provide cellular signals such as those mentioned herein that facilitate tissue regeneration. Finally the scaffold needs to be non-immunogenic so that it is not rejected by the host, and it needs to be non-thrombogenic.

Particular study of the components of the native scaffolds facilitates design of compositions well-suited for regeneration of myocardium.

Collagens, the most abundant components of ECM, are homo- or heterotrimeric molecules whose subunits, the alpha chains, are distinct gene products. To date 34 different alpha chains have been identified. The sequence of the alpha chains contains a variable number of classical Gly-X-Y repetitive motifs which form the collagenous domains and noncollagenous domains. The collagenous portions of 3 homologous or heterologous alpha chains are folded together into a helix with a coiled coil conformation that constitutes the basic structure motif of collagens.

Characteristically, collagens form highly organized polymers. Two main classes of molecules are formed by collagen polymers: the fibril-forming collagens (collagens type I, II, III, V, and XI) and the non-fibrillar collagens that are a more heterogeneous class. Fibril collagen molecules usually have a single collagenous domain repeated the entire length of the molecule, and non-fibrillar collagen molecules have a mixture of collagenous and noncollagenous domains. On this basis several more subgroups of the collagen family are identified: e.g. the basement membrane collagens (IV, VIII, and X). In addition, most all the different types of collagen have a specific distribution. For example, fibril forming collagens are expressed in the interstitial connective tissue. The most abundant component of basement membranes is collagen IV. The multiplexins, collagens XV and XVIII are also localized to the basement membranes.

In the extracellular matrix of the heart, collagen types I and III predominate, together forming fibrils and providing most of the connective material for typing together myocytes and other structures in the myocardium, and thus these molecule types are involved in the transmission of developed mechanical force in the heart. Only collagen types I, II, III, V, and XI self assemble into fibrils, characterized by a triple helix in the collagen molecules. Some collagens form networks, as with the basement membrane, formed by collagen IV. Type III collagen dominates in the wall of blood vessels and hollow intestinal organs and copolymerizes with type I collagen.

Proteoglycans are grouped into several families, and all have a protein core rich in glycosoaminoglycans. They control proliferation, differentiation, and motility. The lecticans interact with hyaluronan and include aggrecan, versican, neurocan, and brevican. Versican stimulates proliferation of fibroblasts and chondrocytes through the presence in the molecule of EGF-like motifs. The second type of proteoglycans have a protein core with leucine-rich repeats, which form a horse shaped protein good for protein-protein interactions. Their glycosoaminoglycan side chains are mostly chondroitin/dermatan sulphate or keratin sulphate. Decorin, biglycan, fibromodulin, and keratocan are members of this family. Decorin is involved in modulation and differentiation of epithelial and endothelial cells. In addition, transforming growth factor beta (TGF beta) interacts with members of this family.

There are part-time proteoglycans, comprising CD44 (a receptor for hyaluronic acid), macrophage colony stimulating factor, amyloid precursor protein and several collagens (IX, XII, XIV, and XVIII).

The last family of proteoglycans is the heparan sulfate proteoglycans, some of which are located in the matrix, and some of which are on cell membranes. Perlecan and agrin are matrix heparan sulfate proteoglycans found in basement membranes. The syndecans and glypicans are membrane-associated heparan sulfate proteoglycans. Syndecans have a heparan sulfate extracellular moiety that binds with high affinity cytokines and growth factors, including fibroblast growth factor (FGF), hepatocyte growth factor (HGF), platelet-derived growth factor (PDGF), heparin-binding epidermal growth factor (HB-EGF), and vascular endothelial growth factor (VEGF). The heparan sulfate proteoglycans have been implicated in modulation of cell migration, proliferation and differentiation in wound healing.

Glycoproteins are also structural proteins of ECM scaffold. The glycoprotein fibronectin (Fn) is a large dimer that attracts stem cells, fibroblasts and endothelial cells to a site of newly forming matrix. Tenascin is a glycoprotein that has Fn repeats and appears during early embryogenesis then is switched off in mature tissue. Tenascin reappears during wound healing. Other glycoprotein components of ECM include elastin that forms the elastic fibers and is a major structural component along with collagen; fibrillins which are a family of proteins consisting almost entirely of endothelial growth factor (EGF)-like domains. Small glycoproteins present in ECM include nidogen/entactin and fibulins I and II.

The glycoprotein laminin is a large protein with three distinct polypeptide chains. Together with type IV collagen, nidogen, and perlecan, laminin is one of the main components of the basement membrane. Laminin isoforms are synthesized by a wide variety of cells in a tissue-specific manner. Laminin I contains multiple binding sites to cellular proteins. Virtually all epithelial cells synthesize laminin, as do small, skeletal, and cardiac muscle, nerves, endothelial cells, bone marrow cells, and neuroretina. Laminins affect nearby cells, by promoting adhesion, cell migration, and cell differentiation. They exert their effects mostly through binding to integrins on cell surfaces. Laminins 5 and 10 occur predominantly in the vascular basement membrane and mediate adhesion of platelets, leukocytes, and endothelial cells.

In addition to the structural matrix proteins just discussed, specific interactions between cells and the ECM are mediated by functional proteins of the ECM, including transmembrane molecules, mainly integrins, some members of the collagen family, some proteoglycans, glycosaminoglycan chains, and some cell-surface associated proteins. These interactions lead to direct or indirect control of cellular activities within the extracellular matrix scaffold such as adhesion, migration, differentiation, proliferation, and apoptosis.

Glycosaminoglycans (GAGs) are glycosylated post-translational molecules derived from proteoglycans. Well known GAGs include heparin, hyaluronic acid, heparan sulfate, and chondroitin sulfate A, B, and C. Heparin chains stimulate angiogenesis, and act as subunits in a proteoglycan to stimulate the angiogenic effects of fibroblast growth factor-2 (FGF-2) (also known as basic FGF or bFGF). Chondroitin sulfate B (demiatan sulfate) interacts with TGF-beta to control matrix formation and remodeling. The proteoglycan form of chondroitin sulfate B regulates the structure of ECM by controlling collagen fibril size, orientation and deposition. Hyaluronic acid is associated with rapid wound healing and organized deposit of collagen molecules in the matrix. It is believed that hyaluronic acid binds TGF-beta1 to inhibit scar formation.

The ECM is also being remodeled constantly in the live animal. The proteins of the ECM are broken down by matrix metalloproteases, and new protein is made and deposited as replacement protein. Collagens are mostly synthesized by the cells comprising the ECM: fibroblasts, myofibroblasts, osteoblasts, and chondrocytes. Some collagens are also synthesized by adjacent parenchymal cells or also covering cells such as epithelial, endothelial, or mesothelial cells.

The extracellular part of integrins bind fibronectin, collagen and laminin, and act primarily as adhesion molecules. Integrin-ligand binding also triggers cascades of activity for cell survival, cell proliferation, cell motility, and gene transcription.

Tenascins include cytotactin (TN-C). Cell surface receptors for tenascins include integrins, cell adhesion molecules of the Ig superfamily, a transmembrane chrondroitin sulfate proteoglycan (phosphacan) and annexin II. TN-C also interacts with extracellular proteins such as fibronectin and the lecticans (the class of extracellular chondroitin sulphate proteoglycans including aggrecan, versican, and brevican).

In addition to direct knowledge of protein cell interaction many of the proteins associated with the ECM can initiate binding to proteins that then activate to bind other proteins or cells, e.g. decorin binds Fn or thrombospondin and causes their cell adhesion promoting activity. Other proteoglycans control the hydration of the ECM and the spacing between the collagen fibrils and network, which is believed to facilitate cell migration. Proteoglycans regulate cell function by controlling growth factor activity, e.g. decorin, biglycan, and fibromodulin bind to isoforms of transforming growth factor beta (TGF beta) and heparin sulfate proteoglycans bind and store fibroblast growth factor.

The matrix metalloproteases (MMPs) break down the collagen molecules in the ECM so that new collagen can be used to remodel and renew the ECM scaffold. It is also believed that the proteolytic activity of MMPs augment the bioavailability of growth factors sequestered within the ECM, and can activate latent secreted growth factors like TGF-beta and IGF from IGFBPs and cell surface growth factor precursors. MMPs can proteolytically cleave cell surface growth factors, cytokines, chemokine receptors and adhesion receptors, and thus participate in controlling responses to growth factors, cytokines, chemokines, as well as cell-cell and cell-ECM interactions.

Structural or functional matrix proteins that can comprise the compositions herein disclosed to facilitate myocardial tissue regeneration include, minimally, collagen I and III, elastin, laminin, CD44, hyaluronan, syndecan, bFGF, HGF, PDGF, VEGF, Fn, tenascin, heparin, heparan sulfate, chondroitin sulfate B, integrins, decorin, and TGF-beta.

Native extracellular matrix scaffolds, and the proteins that form them, are found in their natural environment, the extracellular matrices of mammals. These materials are prepared for use in mammals in tissue grafts procedures. Small intestine submucosa (SIS) is described in U.S. Pat. No. 5,275,826, urinary bladder submucosa (UBS) is described in U.S. Pat. No. 5,554,389, stomach submucosa (SS) is described in U.S. Pat. No. 6,099,567, and liver submucosa (LS) or liver basement membrane (LBM) is described in U.S. Pat. No. 6,379,710, to name some of the extracellular matrix scaffolds presently available for explanting procedures. In addition, collagen from mammalian sources can be retrieved from matrix containing tissues and used to form a matrix composition. Extracellular matrices can be synthesized from cell cultures as in the product manufactured by Matrigel™.

In addition, dermal extracellular matrix material, subcutaneous extracellular matrix material, large intestine extracellular matrix material, placental extracellular matrix material, ornamentum extracellular matrix material, heart extracellular matrix material, and lung extracellular matrix material, may be used, derived and preserved similarly as described herein for the SIS, SS, LBM, and UBM materials. Other organ tissue sources of basement membrane for use in accordance with this invention include spleen, lymph nodes, salivary glands, prostate, pancreas and other secreting glands. In general, any tissue of a mammal that has an extracellular matrix can be used for developing an extracellular matrix component of the invention.

When using collagen-based synthetic ECMs, the collagenous matrix can be selected from a variety of commercially available collagen matrices or can be prepared from a wide variety of natural sources of collagen. Collagenous matrix for use in accordance with the present invention comprises highly conserved collagens, glycoproteins, proteoglycans, and glycosaminoglycans in their natural configuration and natural concentration. Collagens can be from animal sources, from plant sources, or from synthetic sources, all of which are available and standard in the art.

The proportion of scaffold material in the composition when native scaffold used will be large, as the natural balance of extracellular matrix proteins in the native scaffolds usually represents greater than 90% of the extracellular matrix material by dry weight. Accordingly, for a functional tissue regenerative product, the scaffold component of the composition by weight will be generally greater than 50% of the total dry weight of the composition. Most typically, the scaffold will comprise an amount of the composition by weight greater than 60%, greater than 70%, greater than 80%, greater than 82%, greater than 84%, greater than 86%, greater than 88%, greater than 90%, greater than 92%, greater than 94%, greater than 96%, and greater than 98% of the total composition.

Native extracellular matrices are prepared with care that their bioactivity for myocardial tissue regeneration is preserved to the greatest extent possible. Key functions that may need to be preserved include control or initiation of cell adhesion, cell migration, cell differentiation, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, and chemotaxis. Assays for determining these activities are standard in the art. For example, material analysis can be used to identify the molecules present in the material composition. Also, in vitro cell adhesion tests can be conducted to make sure that the fabric or composition is capable of cell adhesion.

The matrices are generally decellularized in order to render them non-immunogenic. A critical aspect of the decellularization process is that the process be completed with some of the key protein function retained, either by replacement of proteins incidentally extracted with the cells, or by adding exogenous cells to the matrix composition after cell extraction, which cells produce or carry proteins needed for the function of tissue regeneration in vivo.

Myocardial tissue has been regenerated in vivo in non-humans using native xenogenic extracellular matrix scaffolds in the form of intact patches derived and prepared from mammals, so it can be presumed that at least some of the components required for myocardial tissue regeneration are to be found in these xenogenic patch matrices. Prudent practice may dictate that the cell extract from the patches be tested for its protein make-up, so that if necessary proteins are removed they can be place back into the matrix composition, perhaps using exogenous proteins at approximately the same amount as those detected in the extraction solution. Replacing lost essential proteins may also be necessary with emulsions or injectable solutions of extracellular matrix, particularly those emulsified from mammalian sources. Another option would be that the proteins extracted during the cell extraction process can simply be added back after the cell extraction is complete, thus preserving the desired bioactivity in the material.

The bioactivity of extracellular matrix material can be mimicked in tissue regeneration experiments with combinations of native and synthetic extracellular matrices explanted together, also optionally with additional components such as proteins or cells, in order to provide an optimal myocardial tissue regenerative composition and environment in vivo. What works as the best composition for myocardial tissue regeneration in patients, particularly humans can be tested first in other mammals by standard explanting procedures to determine whether tissue regeneration is accomplished and optimized by a particular composition. See Badylak, et al, *The Heart Surgery Forum*, Extracellular Matrix for Myocardial Repair, vol. 6(2), pp. 20-26 (2003).

When adding proteins to the extracellular matrix composition, be it an emulsified composition, or another formulation of matrix, the proteins may be simply added with the composition, or each protein may be covalently linked to a molecule in the matrix. Standard protein-molecule linking procedures may be used to accomplish the covalent attachment.

For decellularization when starting with a whole organ, whole organ perfusion process can be used. The organ is perfused with a decellularization agent, for example 0.1% peractic acid rendering the organ acellular. The organ can then be cut into portions and stored (e.g. in aqueous environment, liquid nitrogen, cold, freeze-dried, or vacuum-pressed) for later use. Any appropriate decellularizing agent may be used in whole organ perfusion process.

With regard to submucosal tissue, extractions may be carried out a near neutral pH (in a range from about pH 5.5 to about pH 7.5) in order to preserve the presence of growth factor in the matrices. Alternatively, acidic conditions (i.e. less than 5.5 pH) can be used to preserve the presence of glycosaminoglycan components, at a temperature in a range between 0 and 50 degrees centigrade. In order to regulate the acidic or basic environment for these aqueous extractions, a buffer and chaotropic agent (generally at a concentration from about 2M to about 8M) are selected, such as urea (at a concentration from about 2M to 4M), guanidine (at a concentration from about 2M to about 6M, most typically about 4M), sodium chloride, magnesium chloride, and non-ionic or ionic surfactants. Urea at 2M in pH 7.4 provides extraction of basis FGF and the glycoprotein fibronectin. Using 4M guanidine with pH 7.4 buffer yields a fraction having transforming growth factor beta. (TGF-beta). Accordingly, it may behoove a practitioner to decellularize one portion of a matrix, and extract desired proteins to add back in from other different portions.

Because of the collagenous structure of basement membrane and the desire to minimize degradation of the membrane structure during cell dissociation, collagen specific enzyme activity should be minimized in the enzyme solutions used in the cell-dissociation step. For example, liver tissue is typically also treated with a calcium chelating agent or chaotropic agent such as a mild detergent such as Triton 100. The cell dissociation step can also be conducted using a calcium chelating agent or chaotropic agent in the absence of an enzymatic treatment of the tissue. The cell-dissociation step can be carried out by suspending liver tissue slices in an agitated solution containing about 0.05 to about 2%, more typically about 0.1 to about 1% by weight protease, optionally containing a chaotropic agent or a calcium chelating agent in an amount effective to optimize release and separation of cells from the basement membrane without substantial degradation of the membrane matrix.

After contacting the liver tissue with the cell-dissociation solution for a time sufficient to release all cells from the matrix, the resulting liver basement membrane is rinsed one or more times with saline and optionally stored in a frozen hydrated state or a partially dehydrated state until used as described below. The cell-dissociation step may require several treatments with the cell-dissociation solution to release substantially all cells from the basement membrane. The liver tissue can be treated with a protease solution to remove the component cells, and the resulting extracellular matrix material is further treated to remove or inhibit any residual enzyme activity. For example, the resulting basement membrane can be heated or treated with one or more protease inhibitors.

Basement membrane or other native ECM scaffolds may be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For instance, it is believed that strong gamma radiation may cause loss of strength in the graft material. Preferred sterilization techniques include exposing the graft to peracetic acid, low dose gamma irradiation and gas plasma sterilization; peracetic acid sterilization being the most preferred method.

Synthetic extracellular matrices can be formed using synthetic molecules that polymerize much like native collagen and which form a scaffold environment that mimics the native environment of mammalian extracellular matrix scaffolds. According, such materials as polyethylene terephthalate fiber (Dacron), polytetrafluoroethylene (PTFE), glutaraldehyde-cross linked pericardium, polylactate (PLA), polyglycol (PGA), hyaluronic acid, polyethylene glycol (PEG), polyethelene, nitinol, and collagen from non-animal sources (such as plants or synthetic collagens), can be used as components of a synthetic extracellular matrix scaffold. The synthetic materials listed are standard in the art, and forming hydrogels and matrix-like materials with them is also standard. Their effectiveness can be tested in vivo as sited earlier, by testing in mammals, along with components that typically constitute native ECMs, particularly the growth factors and cells responsive to them.

The ECM-like materials are described generally in the review article "From Cell-ECM Interactions to Tissue Engineering", Rosso, et al., Journal of Cellular Physiology 199: 174-180 (2004). In addition, some ECM-like materials are listed here. Particularly useful biodegradable and/or bioabsorbable polymers include polylactides, poly-glycolides, polycarprolactone, polydioxane and their random and block copolymers. Examples of specific polymers include poly D,L-lactide, polylactide-co-glycolide (85:15) and polylactide-co-glycolide (75:25).

Preferably, the biodegradable and/or bioabsorbable polymers used in the fibrous matrix of the present invention will have a molecular weight in the range of about 1,000 to about 8,000,000 g/mole, more preferably about 4,000 to about 250,000 g/mole. The biodegradable and/or bioabsorbable fiberizable material is preferably a biodegradable and bioabsorbable polymer. Examples of suitable polymers can be found in Bezwada, et al. (1997) Poly(p-Dioxanone) and its copolymers, in Handbook of Biodegradable Polymers, A. J. Domb, J. Kost and D. M. Wiseman, editors, Hardwood Academic Publishers, The Netherlands, pp. 29-61.

The biodegradable and/or bioabsorbable polymer can contain a monomer selected from the group consisting of a glycolide, lactide, dioxanone, caprolactone, trimethylene carbonate, ethylene glycol and lysine. The material can be a random copolymer, block copolymer or blend of monomers, homopolymers, copolymers, and/or heteropolymers that contain these monomers.

The biodegradable and/or bioabsorbable polymers can contain bioabsorbable and biodegradable linear aliphatic polyesters such as polyglycolide (PGA) and its random copolymer poly(glycolide-co-lactide-) (PGA-co-PLA). The FDA has approved these polymers for use in surgical applications, including medical sutures. An advantage of these synthetic absorbable materials is their degradability by simple hydrolysis of the ester backbone in aqueous environments, such as body fluids. The degradation products are ultimately metabolized to carbon dioxide and water or can be excreted via the kidney. These polymers are very different from cellulose based materials, which cannot be absorbed by the body.

Other examples of suitable biocompatible polymers are polyhydroxyalkyl methacrylates including ethylmethacrylate, and hydrogels such as polyvinylpyrrolidone, polyacrylamides, etc. Other suitable bioabsorbable materials are biopolymers which include collagen, gelatin, alginic acid, chitin, chitosan, fibrin, hyaluronic acid, dextran, polyamino acids, polylysine and copolymers of these materials. Any glycosaminoglycan (GAG) type polymer can be used. GAGs can include, e.g., heparin, chondroitin sulfate A or B, and hyaluronic acid, or their synthetic analogues. Any combination, copolymer, polymer or blend thereof of the above examples is contemplated for use according to the present invention. Such bioabsorbable materials may be prepared by known methods.

Nucleic acids from any source can be used as a polymeric biomaterial. Sources include naturally occurring nucleic acids as well as synthesized nucleic acids. Nucleic acids suitable for use in the present invention include naturally occurring forms of nucleic acids, such as DNA (including the A, B and Z structures), RNA (including mRNA, tRNA, and rRNA together or separated) and cDNA, as well as any synthetic or artificial forms of polynucleotides.

The nucleic acids used in the present invention may be modified in a variety of ways, including by cross linking, intra-chain modifications such as methylation and capping, and by copolymerization. Additionally, other beneficial molecules may be attached to the nucleic acid chains. The nucleic acids may have naturally occurring sequences or artificial sequences. The sequence of the nucleic acid may be irrelevant for many aspects of the present invention. However, special sequences may be used to prevent any significant effects due to the information coding properties of nucleic acids, to elicit particular cellular responses or to govern the physical structure of the molecule.

Nucleic acids may be used in a variety of crystalline structures both in finished biomaterials and during their production processes. Nucleic acid crystalline structure may be influenced by salts used with the nucleic acid. For example, Na, K, Bi and Ca salts of DNA all have different precipitation rates and different crystalline structures. Additionally, pH influences crystalline structure of nucleic acids.

The physical properties of the nucleic acids may also be influenced by the presence of other physical characteristics. For instance, inclusion of hairpin loops may result in more elastic biomaterials or may provide specific cleavage sites. The nucleic acid polymers and copolymers produced may be used for a variety of tissue engineering applications including to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part. The polymers may also more specifically be used as sutures, scaffolds and wound dressings. The type of nucleic acid polymer or copolymer used may affect the resulting chemical and physical structure of the polymeric biomaterial.

The extracellular matrix can be emulsified for administration to the defective or absent myocardium. The matrix may also be otherwise liquefied or made into an injectable solution, such as an emulsion, or a liquid, or injectable gel, or semi-gel, other injectable formulation that can be administered with a percutaneous catheter, or other device capable of delivering an injectable formulation.

An emulsion of mammalian or synthetic extracellular matrix material can be accomplished as is standard for tissue or polymer emulsification in general. Generally, the emulsion will be maintained in an emulsified state by control of some component of the composition, for example the pH. Upon delivery of the emulsion the pH is altered to allow the molecules of the matrix to polymerize into a three-dimensional scaffold.

An emulsified extracellular matrix material comprising also cells can have the cultured cells simply added into the matrix emulsion, or the cells may be co-cultured with the matrix for a time before administration to the patient. Standard procedures for culturing or co-culturing cells can be used. In addition, where proteins such as growth factors, or any other protein, including protein forms such as peptides or polypeptides, or protein fragments, are added into the extracellular matrix, the protein molecules may be added into the matrix composition, or the protein molecules may be covalently linked to a molecule in the matrix. The covalent linking of protein to matrix molecules can be accomplished by standard covalent protein linking procedures known in the art. The protein may be covalently linked to one or more matrix molecules. The covalent linking may result in an integration of the protein molecules in the matrix scaffold formation once the emulsion converts from the emulsified form to the scaffold form of the extracellular matrix.

Unlike skeletal myocytes, cardiomyocytes withdraw from cell cycle shortly after birth, and adult mammalian cardiomyocytes lack the potential to proliferate. Therefore, in order to regenerate myocardium, the right cells may have to be added to the composition, or the site, or the right molecules to attract the right cells will have to be added to the composition or the site. Transplantation cell sources for the myocardium include allogenic, xenogenic, or autogenic sources. Accordingly, human embryonic stem cells, neonatal cardiomyocytes, myofibroblasts, mesenchymal cells, autotransplanted expanded cardiomyocytes, and adipocytes can be used as additive components to accompany the scaffold.

Embryonic stem cells begin as totipotent cells, differentiate to pluripotent cells, and then further specialization. They are cultured ex vivo and in the culture dish environment differentiate either directly to heart muscle cells, or to bone marrow cells that can become heart muscle cells. The cultured cells are then transplanted into the mammal, either with the composition or in contact with the scaffold and other components.

Myoblasts are another type of cell that lend themselves to transplantation into myocardium, however, they do not always develop into cardiomyocytes in vivo. Adult stem cells are yet another species of cell that work in the context of tissue regeneration. Adult stem cells are thought to work by generating other stem cells (for example those appropriate to myocardium) in a new site, or they differentiate directly to a cardiomyocyte in vivo. They may also differentiate into other lineages after introduction to organs, such as the heart. The adult mammal provides sources for adult stem cells in circulating endothelial precursor cells, bone marrow-derived cells, adipose tissue, or cells from a specific organ. It is known that mononuclear cells isolated from bone marrow aspirate differentiate into endothelial cells in vitro and are detected in newly formed blood vessels after intramuscular injection. Thus, use of cells from bone marrow aspirate may yield endothelial cells in vivo as a component of the composition.

Other cells which may be employed with the invention are the mesenchymal stem cells administered with activating cytokines. Subpopulations of mesenchymal cells have been shown to differentiate toward myogenic cell lines when exposed to cytokines in vitro.

Once a type of cell is chosen, the number of cells needed is determined. Their function and anticipated change upon implantation, as well as their viability during the process of transplantation need to be considered to determine the number of cells to transplant. Also the mode of transplantation is to be considered: several modes including intracoronary, retrograde venous, transvascular injection, direct placement at the site, thoracoscopic injection and intravenous injection can be used to put the cells at the site or to incorporate them with the composition either before delivery or after delivery to the defective myocardium. In all cases, the mode of delivery and whether the cells are first mixed with the other components of the composition is a decision made based on what will provide the best chance for viability of the cells, and the best opportunity for their continued development into cells that can function in the scaffold in vivo in order to signal and promote tissue regeneration.

The following list includes some of the cells that may be used as additional cellular components of the composition of the invention: a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multipotent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell.

In particular, human embryonic stem cells, fetal cardiomyoctes, mesenchymal stem cells, adipocytes, bone marrow progenitor cells, embryonic stem cells, adult stem cells, or post-natal stem cells together with growth factors or alone with matrix scaffold optimize myocardium regeneration in vivo.

Cells can be seeded directly onto matrix scaffold sheets under conditions conducive to eukaryotic cell proliferation. The highly porous nature of extracellular matrices in particular will allow diffusion of cell nutrients throughout the membrane matrix. Thus, cells can be cultured on or within the matrix scaffold itself. With the emulsified extracellular matrix compositions, or with some of the other formulations, the cells can be co-cultured with the extracellular matrix material before administration of the complete composition to the patient.

In addition to a native ECM scaffold, or a synthetic scaffold, or a mixture of the two, peptides, polypeptides or proteins can be added. Such components include extracellular structural and functional proteins in admixture so as to mimic either heart ECM, or other native ECMs that are capable of regenerating at least some reasonable percentage of the defective myocardium, for example at least 30%, preferably more than 50%. Effective regeneration of the myocardium relies on the extracellular matrix scaffold by its structure and components. Mimicking the native explant material as closely as possible thus optimizes the opportunity for regeneration using a composition comprising some native ECM, albeit treated, but also with additional components.

The peptides, polypeptides or proteins that can be added to the scaffold are: a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

Typically, the additional peptide, polypeptide, or protein component will comprise an amount of the composition by weight selected from the group consisting of greater than 0.1%, greater than 0.5%, greater than 1%, greater than 1.5%, greater than 2%, greater than 4%, greater than 5%, greater than 10%, greater than 12%, greater than 15%, and greater than 20%.

Evaluation of the effectiveness of a particular protein component or combination of components for myocardial tissue regeneration may be accomplished by contacting the composition with defective myocardium in a test animal, for example a dog, pig, or sheep, or other common test mammal. Myocardial tissue regeneration and myocardium contractility are both indicia to measure the success of the composition and procedure, by procedures standard in the art. In addition, a small sampling of the regenerated tissue can be made to determine that new extracellular matrix and new tissue has been made. As to what balance between structural extracellular matrix proteins and functional ones to use in a given composition, nature provides direction. Most ECMs are predominantly made up of structural proteins by dry weight. Thus only a small portion of functional proteins by weight is needed for effective myocardial tissue regeneration.

Peptides, polypeptides or proteins for the composition may be formulated as is standard in the art for the particular class of protein, and that formulation may be added to the extracellular matrix material (of whatever formulation) for delivery into the patient.

Alternatively, the protein molecules may be covalently linked to an appropriate matrix molecule of any of the matrix formulations. Covalent linking of the protein molecules to molecules of the matrix may be accomplished by standard covalent linking methods known in the art.

Some of the proteins required for the composition can be genetically synthesized in vivo with DNA and vector constituents. Thus a vector having a DNA capable of targeted expression of a selected gene can contribute a bioactive peptide, polypeptide, or protein to the composition. Standard in vivo vector gene expression can be employed.

In addition, other additives such as a nutrient, a sugar, a fat, a lipid, an amino acid, a nucleic acid, a ribo-nucleic acid, may provide support to the regenerative process in vivo in the composition. Finally, also a drug, such as a heart regenerating or angiogenesis promoting drug may be also added to the composition, in such a form as, for example, an organic molecule, an inorganic molecule, a small molecule, a drug, or any other drug-like bioactive molecule.

A formulation of extracellular matrix material can be an emulsified or injectable material derived from mammalian or synthetic sources. The extracellular matrix material can be emulsified or made into an injectable formulation by standard procedures in the art, and maintained as an emulsion or injectable until delivered to the patient. Once delivered to the patient, an environment is established (by some change such as a change in pH) so that the extracellular matrix molecules (be they mammalian or synthetic) polymerize to form a matrix scaffold.

Depending on the nature of the scaffold selected, and depending on which additional components are used, the scaffold component and the additional component can be formulated together in the same way, or in different ways that are however but delivery-compatible with each other for delivery purposes. Options for formulation of the scaffold include a solid sheet, multilaminate sheets, a gel, an emulsion, an injectable solution, a fluid, a paste, a powder, a plug, a strand, a suture, a coil, a cylinder, a weave, a strip, a spray, a vapor, a patch, a sponge, a cream, a coating, a lyophilized material, or a vacuum pressed material, all of which are standard in the art.

Formulation of the additional components, when they are not scaffold-like is generally accomplished using some form of an injectable, semi-gel, or emulsified material, although powdered forms may also then be combined with a hydration-promoting solution at delivery. Thus, formulations for the additional components will generally comprise formulations of the nature of a gel, an emulsion, an injectable solution, a fluid, a paste, a spray, a vapor, a cream, and a coating. Dried materials that are hydrated either at delivery or just before delivery are powders, such as lyophilized materials.

Cells can be added in from a culture, or can be co-cultured with the matrix component of the composition. Proteins can be added into the composition, or covalently linked to matrix molecules. DNA can be added in with their vectors for expressing proteins in vivo. Other additives can be combined with the matrix component as is practical for the delivery of the composition (for example, as an injectable or a composition administered with a percutaneous catheter) and as is practical for maintaining bioactivity of the molecules or components in vivo.

Fluidized forms is of native extracellular matrices are described, e.g. in U.S. Pat. No. 5,275,826. The comminuted fluidized tissue can be solubilized by enzymatic digestion including the use of proteases, such as trypsin or pepsin, or other appropriate enzymes such as a collagenase or a glycosaminoglycanase, or the use of a mixture of enzymes, for a period of time sufficient to solubilize said tissue and form a substantially homogeneous solution.

The present invention also contemplates the use of powder forms of extracellular matrix scaffolds. In one embodiment a powder form is prepared by pulverizing basement membrane submucosa tissue under liquid nitrogen to produce particles ranging in size from 0.1 to 1 $mm^2$. The particulate composition is then lyophilized overnight and sterilized to form a solid substantially anhydrous particulate composite. Alternatively, a powder form of basement membrane can be formed from fluidized basement membranes by drying the suspensions or solutions of comminuted basement membrane. The dehydrated forms have been rehydrated and used as cell culture substrates without any apparent loss of their ability to support cell growth.

The mode used for delivery of the compositions of the invention to the defective myocardium may be critical in establishing tissue regeneration in vivo. Standard delivery to myocardial sites can be used for injectable, fluidized, emulsified, gelled, or otherwise semi-fluid materials, such as direct injecting (e.g. with a needle and syringe), or injecting with a percutaneous catheter. For materials that have been rendered wholly or partially vaporized, force-driven delivery of the material can be used, for example, $CO_2$ powering emission of fine emulsion, micronizing an injectable solution, ink jet delivery, spray with a conventional atomizer or spray unit, or other type of vaporized delivery. Some of these vaporized formulations can be delivered using a percutaneous catheter adapted for delivery of a vaporized formulation.

For materials that are essentially solid, such as some of the native or synthetic scaffolds, physically depositing the material will be the most prudent mode of delivery. For example a patch, sponge, strip, weave, or other geometrically defined material form should be placed at the site of deposit either during surgery, or with a percutaneous minimally invasive catheter capable of depositing all or portions of solid material at the site. Preferred modes of delivery will be minimally invasive delivery procedures, which reduce the risk of infection and provide an easier recovery for the patient.

Where the scaffold component is in a different material form than the additional components, care must be taken to orchestrate an effective delivery of both components to the site. For example, where the scaffold is a solid sheet, and cells have been cultured and proteins hydrolyzed, the cells and proteins may be added to the scaffold prior to delivery and the composition is then delivered in surgery. Alternatively, also in surgery, the solid sheet of scaffold may be delivered and the emulsified agents deposited on the sheet before closure. Where both the scaffold component and the additional components can be emulsified, with complete retention of functionality, the composition can be delivered together by direct injection or percutaneous catheter delivery.

In all cases, before a mode is used to treat a patient, the feasibility and effectiveness of any one delivery mode or combination of modes can be tested in a test mammal prior to actual use in humans.

A site of defective myocardium is identified and the appropriate composition of a scaffold component and additional components is made and formulated. The formulated composition is delivered by an appropriate means to the site of defect. The site and mammal are observed and tested for regeneration of the defective myocardium to determine that an effective amount of the composition has been delivered, particularly to observe new tissue growth, and also to determine that the new tissue has the contractility necessary for it to function usefully as myocardium. Tissue growth and contractility can be tested and observed by standard means, for example, as described in Badylak, et al. referenced above.

Goals for contractility in the defective myocardium include observed and measured contractility in an amount measured against contractility of a normal heart selected from the group consisting of greater than 10%, greater than 20%, greater than 30%, greater than 40%, greater than 50%, greater than 60%, greater than 70%, greater than 80%, greater than 90%, and greater than 95% of normal myocardial contractility in vivo.

The method step of contacting the defective myocardium or site of absent myocardium with a composition of the invention can be accomplished by means discussed in the delivery section, including, delivering the composition by injecting, suturing, stapling, injecting with a percutaneous catheter, $CO_2$ powering emission of fine emulsion, micronizing an injectable solution, inkjet delivery, physically depositing a sponge, physically depositing a patch, physical depositing a strip, or physically depositing a formed scaffold of any shape.

A complementary method of use of the compositions of the invention include a method of inducing angiogenesis in myocardium at a site of ischemia by similarly contacting said ischemic myocardium with a composition of the invention in an amount effective to induce angiogenesis in the myocardium at the site of ischemia. Effectiveness can be measured by measuring vascularization at the site, using standard biomedical procedures for such analysis.

EXAMPLES

Example 1

An emulsion of urinary bladder submucosa (UBS) is prepared using standard emulsifying techniques. The emulsion is free of endogenous cells. This preparation is maintained as an emulsion by controlling the pH during storage of the emulsion before it is administered to the patient. In a minimally invasive procedure, a percutaneous catheter device is loaded with sufficient quantity of the emulsified UBS to address a defect in a human heart, the defect having been identified previously by imaging. The catheter is directed to the site of the myocardium in need of tissue regeneration using sonographic or radiographic imaging. Upon contact with the site, the emulsion is released and the catheter is withdrawn. The tissue regeneration process is monitored by sonography for several weeks or months post-delivery of the emulsion.

Example 2

An emulsion of decellularized immunogenic liver basement membrane (LBM) is prepared using standard known techniques. While maintaining the emulsion state of the LBM, adult stem cells are co-cultured with the emulsion using standard stem cell culturing techniques. When the cells are ready, the entire composition is loaded into a catheter for percutaneous delivery to a human patient in need of tissue regeneration at a site of defective or absent myocardium. The emulsion with the co-cultured cells is delivered to the patient: a percutaneous catheter is loaded with the emulsion and directed to the site of the myocardium in need of tissue regeneration using sonographic or radiographic imaging. Upon contact with the site, the emulsion is released and the catheter is withdrawn. The tissue regeneration process is monitored by sonography for several weeks or months post-delivery of the emulsion.

Example 3

An injectable emulsion of decellularized immunogenic stomach submucosa (SS) is prepared using standard known techniques. An aliquot of glycoaminoglycan (GAG) protein is covalently linked to some of the molecules of the matrix emulsion using standard covalent linking procedures for proteins. While maintaining the emulsive state of the SS, bone marrow progenitor cells are co-cultured with the emulsion using standard progenitor cell culturing techniques. An aliquot of transforming growth factor protein is added to the co-culturing composition before delivery to the human in need of myocardial tissue regeneration. The emulsion complete with cells and proteins is loaded into a percutaneous catheter which is directed to the site of the myocardium in need of tissue regeneration using sonographic or radiographic imaging. Upon contact with the site, the emulsion is released and the catheter is withdrawn. The tissue regeneration process is monitored by sonography for several weeks or months post-delivery of the emulsion.

The preceding merely illustrates the principles of the invention. It will be appreciated that those skilled in the art will be able to devise various arrangements which, although not explicitly described or shown herein, embody the principles of the invention and are included within its spirit and scope.

Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof.

Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. It must be noted that as used herein and in the appended claims, the singular forms "a", "an", and "the" include plural referents unless the context clearly dictates otherwise.

All publications cited are incorporated in their entirety. Such publications are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

What is claimed is:

1. An injectable graft composition for myocardial tissue regeneration, said composition comprising acellular heart extracellular matrix (ECM), said ECM comprising endogenous transforming growth factor beta (TGF-β) and fibroblast growth factor-2 (FGF-2), said ECM further comprising an exogenously added glycosaminoglycan (GAG), said GAG comprising at least 0.1% by weight of said composition, said GAG being linked to said ECM, wherein said GAG stimulates angiogenic effects of FGF-2 and interacts with TGF-β to control matrix formation and remodeling, wherein, when said composition is administered to damaged or diseased cardiovascular tissue, said composition induces stem cell proliferation and differentiation of stem cells into cardiomyocytes.

2. The composition of claim 1, wherein said composition further comprises an exogenously added cytokine.

3. An injectable graft composition for myocardial tissue regeneration, said composition comprising acellular stomach submucosa (SS), said SS comprising endogenous transforming growth factor beta (TGF-β) and fibroblast growth factor-2 (FGF-2), said ECM further comprising an exogenously added glycosaminoglycan (GAG), said GAG comprising at least 0.1% by weight of said composition, said GAG being linked to said ECM, wherein said GAG stimulates angiogenic effects of FGF-2 and interacts with TGF-β to control matrix formation and remodeling, wherein, when said composition is administered to damaged or diseased cardiovascular tissue, said composition induces stem cell proliferation and differentiation of stem cells into cardiomyocytes.

4. The composition of claim 3, wherein said composition further comprises an exogenously added cytokine.

5. An injectable graft composition for myocardial tissue regeneration, said composition comprising acellular liver basement submucosa (LBS), said LBS comprising endogenous transforming growth factor beta (TGF-β) and fibroblast growth factor-2 (FGF-2), said ECM further comprising an exogenously added glycosaminoglycan (GAG), said GAG comprising at least 0.1% by weight of said composition, said GAG being linked to said ECM, wherein said GAG stimulates angiogenic effects of FGF-2 and interacts with TGF-β to control matrix formation and remodeling, wherein, when said composition is administered to damaged or diseased cardiovascular tissue, said composition induces stein cell proliferation and differentiation of stein cells into cardiomyocytes.

6. The composition of claim 5, wherein said composition further comprises an exogenously added cytokine.

7. An injectable graft composition for myocardial tissue regeneration, said composition comprising acellular liver basement membrane (LBM), said LBM comprising endogenous transforming growth factor beta (TGF-β) and fibroblast growth factor-2 (FGF-2), said ECM further comprising an exogenously added glycosaminoglycan (GAG), said GAG comprising at least 0.1% by weight of said composition, said GAG being linked to said ECM, wherein said GAG stimulates angiogenic effects of FGF-2 and interacts with TGF-β to control matrix formation and remodeling, wherein, when said composition is administered to damaged or diseased cardiovascular tissue, said composition induces stem cell proliferation and differentiation of stem cells into cardiomyocytes.

8. The composition of claim 7, wherein said composition further comprises an exogenously added cytokine.

9. An injectable graft composition for myocardial tissue regeneration, said composition comprising acellular placental extracellular matrix (ECM), said ECM comprising endogenous transforming growth factor beta (TGF-β) and fibroblast growth factor-2 (FGF-2), said ECM further comprising an exogenously added glycosaminoglycan (GAG), said GAG comprising at least 0.1% by weight of said composition, said GAG being linked to said ECM, wherein said GAG stimulates angiogenic effects of FGF-2 and interacts with TGF-β to control matrix formation and remodeling, wherein, when said composition is administered to damaged or diseased cardiovascular tissue, said composition induces stem cell proliferation and differentiation of stem cells into cardiomyocytes.

10. The composition of claim 9, wherein said composition further comprises an exogenously added cytokine.

* * * * *